(12) United States Patent
Matsumoto

(10) Patent No.: US 11,311,277 B2
(45) Date of Patent: *Apr. 26, 2022

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tsuyoshi Matsumoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 251 days.

This patent is subject to a terminal disclaimer.

(21) Appl. No.: 16/294,288

(22) Filed: Mar. 6, 2019

(65) Prior Publication Data

US 2019/0200963 A1 Jul. 4, 2019

Related U.S. Application Data

(63) Continuation of application No. PCT/JP2017/019410, filed on May 24, 2017.

(30) Foreign Application Priority Data

Sep. 16, 2016 (JP) .............................. JP2016-181715

(51) Int. Cl.
*A61B 8/08* (2006.01)
*A61B 8/14* (2006.01)
*A61B 8/00* (2006.01)

(52) U.S. Cl.
CPC .............. *A61B 8/5207* (2013.01); *A61B 8/08* (2013.01); *A61B 8/14* (2013.01); *A61B 8/463* (2013.01);

(Continued)

(58) Field of Classification Search
CPC ........ A61B 8/4245–4263; A61B 8/085; A61B 8/5207; A61B 8/463
See application file for complete search history.

(56) References Cited

U.S. PATENT DOCUMENTS 9,058,647 B2 * 6/2015 Ishida .................... G06T 7/344
2004/0193053 A1 9/2004 Kato
(Continued)

FOREIGN PATENT DOCUMENTS

CN 105740751 A 7/2016
CN 105451882 A 3/2018
(Continued)

OTHER PUBLICATIONS

International Preliminary Report on Patentability and Written Opinion of the International Searching Authority dated Mar. 28, 2019, for International Application No. PCT/JP2017/019410, with an English Translation of the Written Opinion.

(Continued)

*Primary Examiner* — Catherine B Kuhlman
*Assistant Examiner* — Andrew W Begeman
(74) *Attorney, Agent, or Firm* — Birch, Stewart, Kolasch & Birch, LLP

(57) ABSTRACT

An ultrasound diagnostic apparatus has: an image acquiring unit that transmits/receives an ultrasound beam from an ultrasound probe to acquire an ultrasound image; a part probability calculating unit that calculates, for the ultrasound image acquired in accordance with a first imaging condition, a probability that a part included in the ultrasound image is a specific part from at least one of an orientation angle of the ultrasound probe or an analysis result of the ultrasound image; and an imaging condition changing unit that changes, when the probability is greater than or equal to a threshold value, the first imaging condition to a second (Continued)

imaging condition for identifying the part for which the probability has been calculated, in which an ultrasound image is further acquired by using the second imaging condition.

16 Claims, 7 Drawing Sheets

(52) U.S. Cl.
CPC .............. *A61B 8/5223* (2013.01); *A61B 8/54* (2013.01); *A61B 8/4254* (2013.01); *A61B 8/4444* (2013.01); *A61B 8/4488* (2013.01); *A61B 8/469* (2013.01)

(56) References Cited

U.S. PATENT DOCUMENTS

| | | |
|---|---|---|
| 2007/0055153 A1 | 3/2007 | Simopoulos et al. |
| 2007/0239006 A1 | 10/2007 | Kamiyama et al. |
| 2008/0154123 A1 | 6/2008 | Jackson et al. |
| 2012/0203106 A1 | 8/2012 | Matsunaga et al. |
| 2013/0184584 A1 | 7/2013 | Berkey |
| 2014/0187946 A1* | 7/2014 | Miller ................ A61B 8/54 600/440 |
| 2015/0209006 A1 | 7/2015 | Kawagishi et al. |
| 2016/0074017 A1 | 3/2016 | Lee |
| 2018/0042577 A1* | 2/2018 | Perrey .................. A61B 8/483 |

FOREIGN PATENT DOCUMENTS

| | | |
|---|---|---|
| EP | 2926736 A1 | 10/2015 |
| JP | 4-224738 A | 8/1992 |
| JP | 2004-290404 A | 10/2004 |
| JP | 2010-259662 A | 11/2010 |
| JP | 2013-111309 A | 6/2013 |
| JP | 2014-213030 A | 11/2014 |

OTHER PUBLICATIONS

International Search Report, dated Jul. 18, 2017, for International Application No. PCT/ JP2017/019410, with an English translation.
Extended European Search Report, dated Sep. 17, 2019, for European Application No. 17850485.8.
Chinese Office Action and Search Report, dated Apr. 6, 2021, for Chinese Application No. 201780056223.1, with an English translation of the Chinese Office Action.
Chinese Office Action and Search Report for Chinese Application No. 201780056223.1, dated Sep. 7, 2021, with English translation of the Office Action.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2017/019410 filed on May 24, 2017, which claims priority under 35 U.S.C. § 119(a) to Japanese Patent Application No. 2016-181715 filed on Sep. 16, 2016. The above application is hereby expressly incorporated by reference, in its entirety, into the present application.

BACKGROUND OF THE INVENTION

1. Field of the Invention

The present invention relates to an ultrasound diagnostic apparatus and a control method of the ultrasound diagnostic apparatus, and particularly to an ultrasound diagnostic apparatus that identifies a part of a subject for which an ultrasound image has been generated.

2. Description of the Related Art

In the related art, ultrasound diagnostic apparatuses have been known as apparatuses that obtain images of the inside of subjects by applying a transducer array on the subjects. A typical ultrasound diagnostic apparatus transmits an ultrasound beam from the transducer array, in which a plurality of elements are arranged, toward the inside of a subject and receives ultrasound echoes from the subject in the transducer array to acquire element data. Further, the ultrasound diagnostic apparatus performs electrical processing on the obtained element data to obtain an ultrasound image of the relevant part of the subject.

In a case of making a diagnosis of a subject by using such an ultrasound diagnostic apparatus, in order to obtain an ultrasound image that is appropriate for a diagnosis of each testing part, an operator sets an imaging condition in accordance with a part to be captured. In this case, every time the part to be captured is changed, the operator needs to set the imaging condition. Thus, JP2004-290404A discloses an ultrasound diagnostic apparatus that stores an ultrasound image captured by using the imaging condition set by the operator as a reference image together with the imaging condition at the time of capturing the image, and that reads and sets the imaging condition of the reference image at the time of capturing an image of a part corresponding to the reference image.

SUMMARY OF THE INVENTION

By the way, for example, in eFAST (extended Focused Assessment with Sonography for Trauma) testing in which a plurality of diagnostic parts are successively diagnosed for an initial diagnosis of a wound patient in emergency, in many cases, an ultrasound diagnosis is made by using a general imaging condition as an initial condition for the plurality of diagnostic parts. Therefore, for example, in the eFAST testing, the amount of information for identifying each diagnostic part obtained from a generated ultrasound image is small, and it has been difficult to finely identify the diagnostic part.

In addition, in this case, with the techniques disclosed in JP2004-290404A, means for identifying the diagnostic part is not present. Thus, in a case where the diagnostic part is unknown, it has been difficult to select a reference image that is appropriate for the diagnostic part, that is, to select an imaging condition that is appropriate for the diagnostic part.

The present invention has been made to solve such problems of the related art, and an object is to provide an ultrasound diagnostic apparatus that can finely identify a diagnostic part and a control method of the ultrasound diagnostic apparatus.

In order to achieve the above object, an ultrasound diagnostic apparatus according to the present invention has: an ultrasound probe; an image acquiring unit that transmits an ultrasound beam from the ultrasound probe toward a subject and receives the ultrasound beam in accordance with a set imaging condition to acquire an ultrasound image; a part probability calculating unit that calculates, for the ultrasound image acquired in the image acquiring unit in accordance with a first imaging condition, a probability that a part of the subject included in the ultrasound image is a specific part from at least one of an orientation angle of the ultrasound probe or an analysis result of the ultrasound image; and an imaging condition changing unit that changes, when the probability calculated in the part probability calculating unit is greater than or equal to a predetermined threshold value, the first imaging condition to a second imaging condition for identifying the part for which the probability has been calculated, in which the image acquiring unit further acquires an ultrasound image by using the second imaging condition.

In addition, it is preferable that the ultrasound diagnostic apparatus further have an orientation sensor that detects an operation or a position of the ultrasound probe; and a probe orientation angle detecting unit that detects the orientation angle on the basis of a signal of the orientation sensor, in which the part probability calculating unit calculates the probability on the basis of the orientation angle.

In addition, it is preferable that the ultrasound diagnostic apparatus further have an image analyzing unit that analyzes the ultrasound image further acquired in the image acquiring unit.

Alternatively, the ultrasound diagnostic apparatus may further have an image analyzing unit that analyzes the ultrasound image acquired in the image acquiring unit, in which the part probability calculating unit calculates the probability on the basis of the analysis result in the image analyzing unit.

Alternatively, the ultrasound diagnostic apparatus may further have an image analyzing unit that analyzes the ultrasound image acquired in the image acquiring unit; an orientation sensor that detects an operation or a position of the ultrasound probe; and a probe orientation angle detecting unit that detects the orientation angle on the basis of a signal of the orientation sensor, in which the part probability calculating unit calculates the probability on the basis of the orientation angle and the analysis result of the ultrasound image in the image analyzing unit.

In addition, it is preferable that the part probability calculating unit calculate the probability on the basis of a result of image analysis of an ultrasound image of a single frame in the image analyzing unit.

Alternatively, the part probability calculating unit may calculate the probability on the basis of a result of analysis of a movement of a specific pattern included in ultrasound images of a plurality of frames in common in the image analyzing unit.

In addition, it is preferable that the ultrasound diagnostic apparatus further have a part identifying unit that identifies a part of a subject for which the probability has been calculated on the basis of the analysis result of the ultrasound image in the image analyzing unit, the ultrasound image being further acquired in the image acquiring unit.

In addition, in a control method of an ultrasound diagnostic apparatus according to the present invention, an ultrasound beam is transmitted from an ultrasound probe toward a subject and is received in accordance with a set imaging condition to acquire an ultrasound image; for the ultrasound image acquired in accordance with a first imaging condition, a probability that a part of the subject included in the ultrasound image is a specific part is calculated from at least one of an orientation angle of the ultrasound probe or an analysis result of the ultrasound image; when the calculated probability is greater than or equal to a predetermined threshold value, the first imaging condition is changed to a second imaging condition for identifying the part for which the probability has been calculated; and an ultrasound image is further acquired by using the second imaging condition.

According to the present invention, the ultrasound diagnostic apparatus has the imaging condition changing unit that changes, on the basis of the probability calculated by the part probability calculating unit, the first imaging condition to the second imaging condition for identifying the part for which the probability has been calculated, and thus, even in a case where an ultrasound image is generated by using an imaging condition with which it is difficult to identify a diagnostic part in the ultrasound diagnostic apparatus, it is possible to finely identify the diagnostic part.

DESCRIPTION OF THE PREFERRED EMBODIMENTS

Hereinafter, embodiments of the invention will be described with reference to the attached drawings.

First Embodiment

Figure 1:
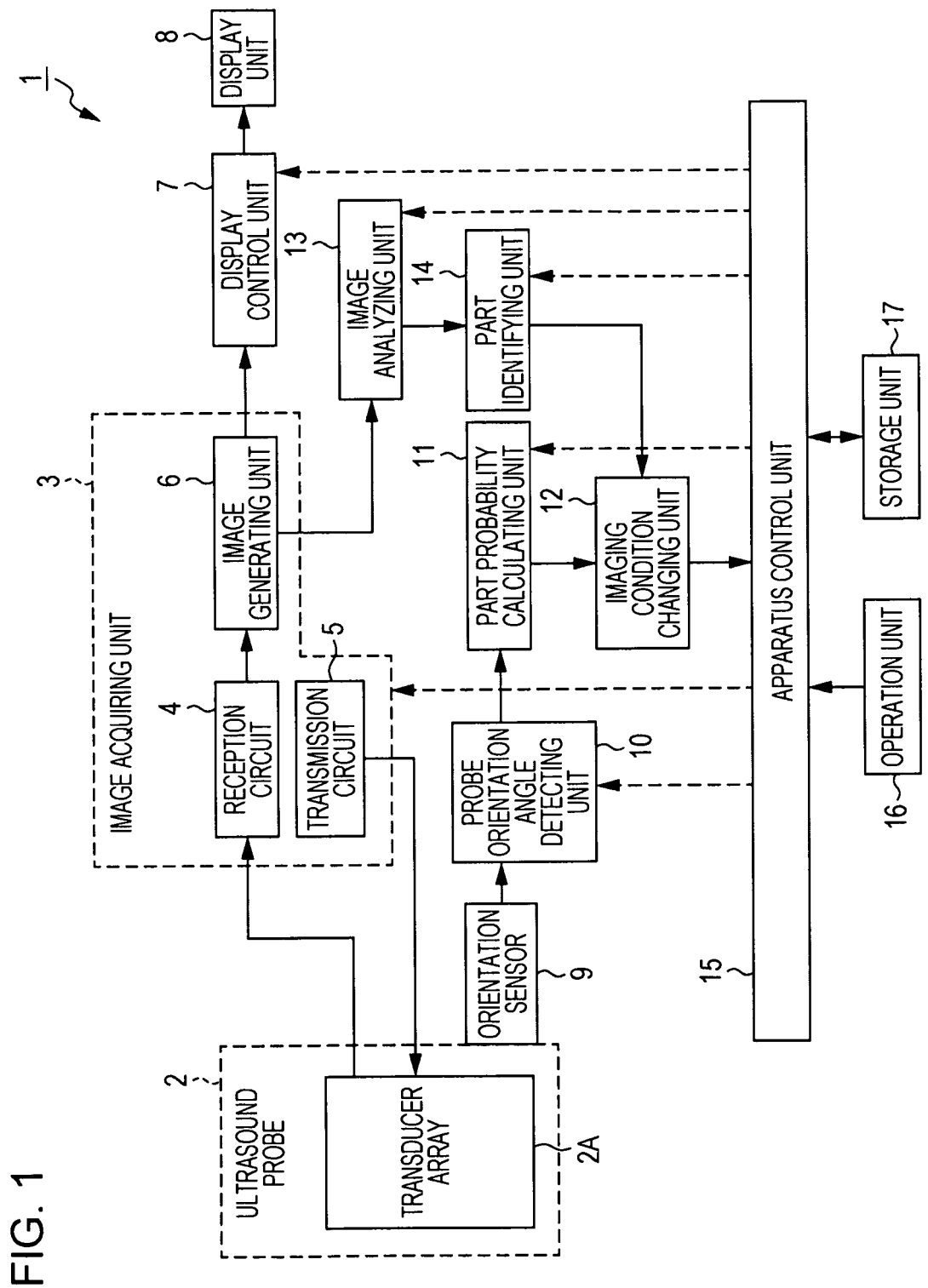
FIG. 1 is a block diagram illustrating a configuration of an ultrasound diagnostic apparatus according to a first embodiment of the present invention.

FIG. 1 illustrates a configuration of an ultrasound diagnostic apparatus according to a first embodiment of the present invention. An ultrasound diagnostic apparatus 1 includes an ultrasound probe 2 in which a transducer array 2A is incorporated, and a display control unit 7 and a display unit 8 are sequentially connected to the ultrasound probe 2 via an image acquiring unit 3.

The image acquiring unit 3 has a reception circuit 4 and a transmission circuit 5 that are to be connected to the transducer array 2A of the ultrasound probe 2 and an image generating unit 6 that is connected to the reception circuit 4, and the display control unit 7 is connected to the image generating unit 6. In addition, the ultrasound probe 2 includes an orientation sensor 9, and a probe orientation angle detecting unit 10 is connected to the orientation sensor 9. Further, a part probability calculating unit 11 and an imaging condition changing unit 12 are sequentially connected to the probe orientation angle detecting unit 10. In addition, an image analyzing unit 13 is connected to the image generating unit 6 of the image acquiring unit 3, a part identifying unit 14 is connected to the image analyzing unit 13, and the imaging condition changing unit 12 is connected to the part identifying unit 14.

Further, an apparatus control unit 15 is connected to the image acquiring unit 3, the display control unit 7, the probe orientation angle detecting unit 10, the part probability calculating unit 11, the imaging condition changing unit 12, the image analyzing unit 13, and the part identifying unit 14, and an operation unit 16 and a storage unit 17 are each connected to the apparatus control unit 15. Note that the apparatus control unit 15 and the storage unit 17 are connected in such a manner that information can be mutually transferred.

The transducer array 2A of the ultrasound probe 2 illustrated in FIG. 1 has a plurality of elements (ultrasound transducers) that are arranged one-dimensionally or two-dimensionally. These elements each transmit an ultrasound in accordance with a driving signal supplied from the transmission circuit 5 and also receive ultrasound echoes from a subject to output a reception signal. Each of the elements is constituted by using, for example, a transducer in which electrodes are formed at both ends of a piezoelectric material formed of piezoelectric ceramic typified by PZT (Lead Zirconate Titanate), a high molecular piezoelectric element typified by PVDF (Poly Vinylidene Di Fluoride), a piezoelectric single crystal typified by PMN-PT (Lead Magnesium Niobate-Lead Titanate), or the like.

When a pulsed or continuous-wave voltage is applied to the electrodes of such transducers, the piezoelectric material stretches or compresses, and a pulsed or continuous-wave ultrasound is generated from each of the transducers, and a composite wave of these ultrasounds form an ultrasound beam. In addition, by receiving a propagating ultrasound, the respective transducers stretch and compress to generate electric signals, and these electric signals are output as an ultrasound reception signal from the respective transducers to the reception circuit 4.

Figure 2:
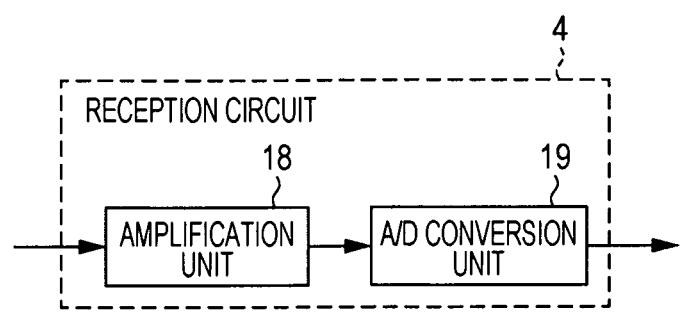
FIG. 2 is a block diagram illustrating an internal configuration of a reception circuit used in the first embodiment.

As illustrated in FIG. 2, the reception circuit 4 of the image acquiring unit 3 has a configuration in which an amplification unit 18 and an A/D (Analog/Digital) conversion unit 19 are connected in series. The reception circuit 4 amplifies the reception signal output from each of the elements of the transducer array 2A in the amplification unit 18, and outputs element data obtained by digitalizing the reception signal in the A/D conversion unit 19 to the image generating unit 6.

The transmission circuit 5 includes, for example, a plurality of pulse generators, and on the basis of a transmission delay pattern selected in accordance with a control signal from the apparatus control unit 15, adjusts a delay amount of each driving signal in such a manner that ultrasounds transmitted from the plurality of elements of the transducer array 2A form an ultrasound beam, and supplies the driving signal to the plurality of elements.

Figure 3:
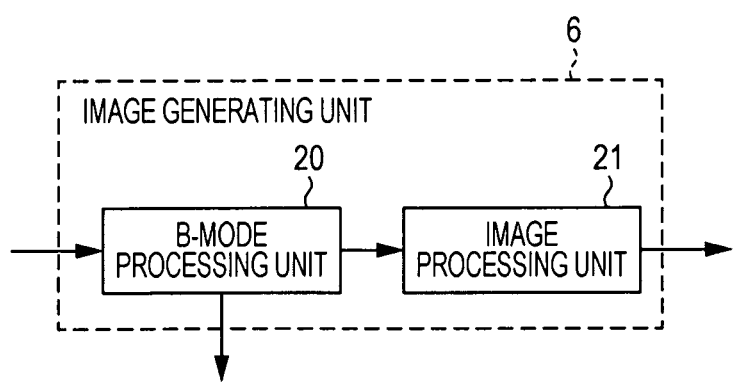
FIG. 3 is a block diagram illustrating an internal configuration of an image generating unit used in the first embodiment.

The image generating unit 6 of the image acquiring unit 3 has a configuration in which, as illustrated in FIG. 3, a B-mode (Brightness mode) processing unit 20 and an image processing unit 21 are sequentially connected in series. On the basis of a reception delay pattern selected in accordance with a control signal from the apparatus control unit 15, the B-mode processing unit 20 performs reception focus processing in which each element data item in accordance with a set sound speed is given a corresponding delay and addition (phasing addition) is performed. Through this reception focus processing, a sound ray signal in which a focus of ultrasound echoes is narrowed is generated. Further, the B-mode processing unit 20 performs, on the sound ray signal, correction of attenuation due to a propagating distance in accordance with a depth of a reflection position of the ultrasound wave, and then performs envelope detection processing to generate a B-mode image signal, which is sectional-layer image information regarding tissues in the subject. The B-mode image signal generated in the B-mode processing unit 20 is output to the display control unit 7 or the image analyzing unit 13.

The image processing unit 21 converts the B-mode image signal generated in the B-mode processing unit 20 to an image signal according to a scan method of a typical television signal (performs raster conversion) and performs various kinds of necessary image processing, such as tone processing on the B-mode image signal, and then outputs the B-mode image signal to the display control unit 7.

As illustrated in FIG. 1, on the basis of the B-mode image signal acquired in the image acquiring unit 3, the display control unit 7 of the ultrasound diagnostic apparatus 1 causes the display unit 8 to display an ultrasound diagnostic image.

The display unit 8 includes, for example, a display apparatus such as an LCD (Liquid Crystal Display) and displays an ultrasound diagnostic image under control of the apparatus control unit 15.

The orientation sensor 9 is included in the ultrasound probe 2 and detects, as an electric signal, an operation or a position of the ultrasound probe 2 that is operated by an operator during an ultrasound diagnosis.

The orientation sensor 9 is not particularly limited as long as the operation or the position of the ultrasound probe 2 can be detected. However, in the following description, a case where an acceleration sensor that detects the operation of the ultrasound probe 2 is used as the orientation sensor 9 will be described. In this case, the orientation sensor 9 detects, as the electric signal, acceleration of three components along three axes that intersect with one another in a three-dimensional space. Further, the signal detected by the orientation sensor 9 is output to the probe orientation angle detecting unit 10.

On the basis of the signal indicating the operation of the ultrasound probe 2 detected by the orientation sensor 9, the probe orientation angle detecting unit 10 detects an orientation angle of the ultrasound probe 2. For example, from the acceleration in the three-dimensional space obtained in the orientation sensor 9, the orientation angle of the ultrasound probe 2 can be calculated by using a known calculation method.

When an operator makes an ultrasound diagnosis by using the ultrasound probe 2, on the basis of the orientation angle of the ultrasound probe 2 detected in the probe orientation angle detecting unit 10, the part probability calculating unit 11 calculates a probability (part probability) that a part of the subject included in the ultrasound image acquired in the image acquiring unit 3 is a specific part. The part probability calculating unit 11 can calculate, for example, a probability that the part of the subject included in the ultrasound image acquired in the image acquiring unit 3 is a heart. Note that the calculation of the part probability in the part probability calculating unit 11 will be described later in detail.

The imaging condition changing unit 12 changes an imaging condition used when the ultrasound image is acquired in the image acquiring unit 3 to an imaging condition in accordance with the part where the ultrasound diagnosis has been made. The imaging condition here includes a frame rate at the time of an ultrasound diagnosis, a resolution of the ultrasound image, brightness of the ultrasound image, and a dynamic range at the time of the ultrasound diagnosis. The imaging condition changing unit 12 changes at least one condition among these imaging conditions on the basis of a calculation result of the part probability in the part probability calculating unit 11 or a result of identification of a part in the part identifying unit 14.

The image analyzing unit 13 performs movement analysis and image analysis such as pattern recognition on the B-mode image signal generated in the B-mode processing unit 20 of the image generating unit 6 of the image acquiring unit 3 and outputs a result of the image analysis to the part identifying unit 14.

On the basis of a result of the analysis of the ultrasound image in the image analyzing unit 13, the part identifying unit 14 identifies the part of the subject included in the ultrasound image and outputs information on the identified part to the imaging condition changing unit 12.

On the basis of an instruction that has been input by an operator through the operation unit 16, the apparatus control unit 15 controls each unit of the ultrasound diagnostic apparatus 1.

The operation unit 16 is used by the operator to perform an input operation and can be configured to include a keyboard, a mouse, a trackball, a touch panel, and the like.

The storage unit 17 stores an operation program of the ultrasound diagnostic apparatus 1 and the like and can be a recording medium such as an HDD (Hard Disc Drive), an SSD (Solid State Drive), an FD (Flexible Disc), an MO disc (Magneto-Optical disc), an MT (Magnetic Tape), a RAM (Random Access Memory), a CD (Compact Disc), a DVD (Digital Versatile Disc), an SD card (Secure Digital card), or a USB memory (Universal Serial Bus memory), a server, or the like.

Note that the image generating unit 6, the display control unit 7, the probe orientation angle detecting unit 10, the part probability calculating unit 11, the imaging condition changing unit 12, the image analyzing unit 13, and the part identifying unit 14 are configured from a CPU (Central Processing Unit) and an operation program for causing the CPU to perform various kinds of processing. However, these units may also be configured by using a digital circuit. In addition, these image generating unit 6, the display control unit 7, the probe orientation angle detecting unit 10, the part probability calculating unit 11, the imaging condition changing unit 12, the image analyzing unit 13, and the part identifying unit 14 can also be configured to be partly or generally integrated with one CPU.

Next, an operation of the ultrasound diagnostic apparatus 1 in the first embodiment will be described with reference to a flowchart illustrated in FIG. 4.

First, in step S1, the apparatus control unit 15 initializes an imaging condition for acquiring an ultrasound image in the image acquiring unit 3 to a first imaging condition. The first imaging condition is, for example, an imaging condition for which a general setting is set for a plurality of diagnostic parts. Such a general imaging condition for a plurality of diagnostic parts is set in many cases in such a manner that, for example, a plurality of parts can be diagnosed rapidly in a continuous diagnosis such as eFAST testing.

In step S2, under the first imaging condition, the reception circuit 4 and the transmission circuit 5 of the image acquiring unit 3 transmits/receives and passes an ultrasound beam by using a plurality of ultrasound transducers of the transducer array 2A of the ultrasound probe 2. At this time, a reception signal is output to the reception circuit 4 from each of the ultrasound transducers that have received ultrasound echoes from the subject, and the reception signal is amplified and subjected to A/D conversion in the amplification unit 18 and the A/D conversion unit 19 of the reception circuit 4 so that the reception signal is generated. In addition, while the ultrasound beam is transmitted/received and passed, the orientation sensor 9 detects the operation of the ultrasound probe 2 that is being operated by an operator as an electric signal.

The following step S3 and step S4 are performed in synchronization and in parallel.

In step S3, the B-mode processing unit 20 of the image generating unit 6 sequentially generates B-mode images by using reception signals that have been input from the reception circuit 4 on the basis of a frame rate at the time of acquiring the ultrasound images, which is set in the first imaging condition.

In addition, in step S4, on the basis of an electric signal representing the operation of the ultrasound probe 2, the electrical signal having been input from the orientation sensor 9, the probe orientation angle detecting unit 10 detects an orientation angle of the ultrasound probe 2 at the time of transmission/reception or passing of an ultrasound beam performed in step S2. For example, from the acceleration of three components along three axes that intersect with one another in a three-dimensional space, which has been detected by the orientation sensor 9, the orientation angle of the ultrasound probe 2 can be calculated by using a known calculation method. The orientation angle of the ultrasound probe 2 differs depending on the part of the subject for which the ultrasound diagnosis is made. For example, in eFAST testing, the diagnostic part can be a heart, lungs, a right abdomen, a left abdomen, or a urinary bladder. In order to conduct appropriate testing on these parts, it is known that the ultrasound probe 2 is used at a different orientation angle depending on the part. In addition, in the ultrasound diagnosis of a plurality of parts, for example, in an abdomen diagnosis, an operator makes a diagnosis while moving the ultrasound probe 2 in many cases. In the above manner, in a case where the operator moves the ultrasound probe 2 during the ultrasound diagnosis, the probe orientation angle detecting unit 10 can detect, for example, an average value of the orientation angle of the ultrasound probe 2 within a fixed period of time as the orientation angle of the ultrasound probe 2.

The generation of a B-mode image in step S3 and the detection of the orientation angle of the ultrasound probe 2 in step S4 are started at the same time by simultaneously transmitting, to the image acquiring unit 3 and the probe orientation angle detecting unit 10 from the apparatus control unit 15, information indicating that the B-mode image generation is to be started and information indicating that the orientation angle detection is to be started. In response to the start of the generation of the B-mode image and the detection of the orientation angle of the ultrasound probe 2 in step S3 and step S4, the frame rate that is set in the first imaging condition and a sampling frequency for the probe orientation angle detecting unit 10 to sample a signal of the orientation sensor 9 are synchronized. In the above manner, the generation of the B-mode image in step S3 and the detection of the orientation angle of the ultrasound probe 2 in step S4 are performed in synchronization and in parallel. Note that, for example, by thinning out information of the orientation sensor at a frequency higher than the frame rate that is set in the first imaging condition, the frame rate that is set in the first imaging condition and the sampling frequency of the probe orientation angle detecting unit 10 can correspond to each other.

In step S5, from the orientation angle of the ultrasound probe 2 detected by the probe orientation angle detecting unit 10 in step S4, the part probability calculating unit 11 calculates a probability (part probability) that the part of the subject included in the B-mode image (ultrasound image) generated by the B-mode processing unit 20 of the image generating unit 6 in step S3 is a specific part. Although various calculation methods can be used for the calculation of the part probability in the part probability calculating unit 11, for example, the part probability calculating unit 11 can calculate, as the part probability, a reciprocal of a difference between a target orientation angle of the ultrasound probe 2 (target probe angle) for a specific part of the subject and the actual orientation angle detected by the probe orientation angle detecting unit 10. In this case, by using the target probe angle for each part of the subject, the part probability calculating unit 11 calculates each part probability that the part included in the ultrasound image is the specific part.

In step S6, the apparatus control unit 15 determines whether the part probability calculated by the part probability calculating unit 11 by using the orientation angle of the ultrasound probe 2 is greater than or equal to a predetermined threshold value. For example, in a case where the part probability calculating unit 11 calculates the probabilities that the part included in the ultrasound image generated in step S3 is a heart, lungs, a right abdomen, a left abdomen, and a urinary bladder, it is determined whether these part probabilities are each greater than or equal to the threshold value. The threshold value used for the determination of the part probability is preferably a value at which only the part probabilities for parts where the orientation angles of the ultrasound probe 2 at the time of the ultrasound diagnosis, that is, the target probe angles, are similar are greater than or equal to the threshold value.

Note that this threshold value can be decided by, for example, calculating a statistical value for the orientation angle of the ultrasound probe 2 in previous diagnoses, pretesting, or the like.

If the apparatus control unit 15 determines in step S6 that at least one part probability among the plurality of part probabilities calculated by the part probability calculating unit 11 is greater than or equal to the threshold value, the process proceeds to step S7. In step S7, on the basis of the part probability that is determined by the apparatus control unit 15 to be greater than or equal to the threshold value, the imaging condition changing unit 12 changes the first imaging condition to a second imaging condition for identifying the part for which the part probability has been calculated. For example, if it is determined in step S6 that the part probability that the part included in the ultrasound image is the heart is greater than or equal to the threshold value and that the part probability that the part included in the ultrasound image is the right abdomen is greater than or equal to the threshold value, the imaging condition changing unit 12 changes the first imaging condition to the second imaging condition for identifying the part included in the ultrasound image as either of the heart and the right abdomen. In this case, for example, as the second imaging condition, a condition in which a frame rate at the time of the ultrasound diagnosis is increased for increasing an accuracy of sampling of the beats of a heart can be set.

If the apparatus control unit 15 determines in step S6 that the plurality of part probabilities calculated by the part probability calculating unit 11 are all less than the threshold value, the process proceeds to step S16. In step S16, the apparatus control unit 15 determines whether the number of times the apparatus control unit 15 determines in step S6 that the plurality of part probabilities are all less than the threshold value is N. If the number of times the apparatus control unit 15 determines that the plurality of part probabilities are all less than the threshold value is less than N, the process returns to step S2, and an ultrasound image is acquired by using the first imaging condition. Subsequently, when the number of times of determination that the plurality of part probabilities are all less than the threshold value becomes N, the process proceeds to step S17. A message indicating that an error has occurred is displayed in the display unit 8, and then the ultrasound diagnostic apparatus 1 terminates the operation.

Note that N is a natural number of greater than or equal to 1 and can be set in advance in a program or the like of the ultrasound diagnostic apparatus 1. However, in some cases, the ultrasound image is preferably acquired again as in a case where an operator fails to generate the ultrasound image by using the ultrasound diagnostic apparatus 1, and thus, N is preferably a number of greater than or equal to 2.

In step S8 subsequent to step S7, by using the second imaging condition, the reception circuit 4 and the transmission circuit 5 of the image acquiring unit 3 further transmits/receives and passes an ultrasound beam to/from a part of the subject.

Further, in step S9, the B-mode processing unit 20 of the image generating unit 6 of the image acquiring unit 3 further generates a B-mode image (ultrasound image) signal by using an ultrasound reception signal acquired by using the second imaging condition.

In step S10, the image analyzing unit 13 performs image analysis on the ultrasound image further generated by the B-mode processing unit 20 of the image generating unit 6 in order to identify the part of the subject included in the ultrasound image. For example, in a case where a high frame rate at the time of the ultrasound diagnosis is set as the second imaging condition, the image analyzing unit 13 can perform optical flow, which is time-series image analysis, as the image analysis. Although not illustrated, the optical flow is a technique for mapping a direction and distance of movement of each pattern by using a vector or the like for a plurality of characteristic patterns in the same part included in ultrasound images of a plurality of frames in common by using the ultrasound images of a plurality of frames acquired by the image acquiring unit 3 in a time-series manner. By using such a time-series analysis method, for example, it can become easier to identify a part with much movement such as the heart and a part with a little movement such as the abdomen.

In step S11, on the basis of an analysis result of the ultrasound image in the image analyzing unit 13, the part identifying unit 14 identifies the part of the subject included in the ultrasound image. For example, in a case where the part probabilities determined in step S6 to be greater than or equal to the threshold value are the part probability that the part included in the ultrasound image is the heart and the part probability that the part included in the ultrasound image is the right abdomen and where the image analyzing unit 13 performs image analysis using the optical flow, the part is identified on the basis of the number of vectors mapped in the ultrasound image. That is, the part identifying unit 14 identifies the part as the heart if the number of mapped vectors is greater than or equal to a determined fixed value and identifies the part as the right abdomen if the number of mapped vectors is less than the fixed value.

In step S12, the imaging condition changing unit 12 changes the second imaging condition to a third imaging condition that is appropriate for the part identified by the part identifying unit 14.

In the subsequent step S13, by using the third imaging condition, the reception circuit 4 and the transmission circuit 5 of the image acquiring unit 3 transmits/receives and passes an ultrasound beam to/from the part identified by the part identifying unit 14.

Further, in step S14, by using the third imaging condition, the image generating unit 6 of the image acquiring unit 3 generates a B-mode image signal from a reception signal acquired by the reception circuit 4 and the transmission circuit 5.

In step S15, the apparatus control unit 15 determines whether the part of the subject for which the ultrasound diagnosis is currently being performed has been changed. For example, when the diagnostic part transitions from the heart to the lungs, it is determined that the diagnostic part has been changed. Specifically, in a case where the diagnostic part is changed, the probe typically is released from the surface of the body and radiation is performed to the air, and thus, by the detection of such radiation-to-the-air state (a state where a reflection signal is not obtained), it can be determined that the diagnostic part has been changed. If it is determined in step S15 that the diagnostic part has not been changed, that is, that the same diagnostic part is being diagnosed, the process returns to step S13, and the ultrasound image is acquired by using the third imaging condition. On the other hand, if it is determined in step S15 that the diagnostic part has been changed, the process returns to step S1, and the third imaging condition is initialized to the first imaging condition.

As described above, according to the ultrasound diagnostic apparatus 1 in the first embodiment illustrated in FIG. 1, the ultrasound image is acquired by using the first imaging condition in order to calculate the part probability on the basis of the orientation angle of the ultrasound probe 2, and then the first imaging condition is changed to the second imaging condition to further acquire the ultrasound image in order to identify the part included in the ultrasound image on the basis of the calculated part probability. In the above manner, by acquiring the ultrasound image twice separately, candidate parts for identification can be narrowed down, and thus, the part can be finely identified so as to set an appropriate imaging condition. In addition, the data processing amount of the ultrasound diagnostic apparatus 1 is small compared with the identification of a part using only pattern identification referring to a database, which has been widely performed in the related art, and the period of time for image analysis can be shortened when identifying the part included in the ultrasound image. Further, also in a case where an ultrasound image of a plurality of parts is acquired by using a general imaging condition as the first imaging condition, on the basis of a determination result of the part probability in step S6, the first imaging condition can be changed to the second imaging condition for identifying the candidate parts for identification, and thus, the ultrasound diagnostic apparatus 1 can accurately identify the part.

In addition, the B-mode image is generated in step S3 and the orientation angle of the ultrasound probe 2 is acquired in step S4 in synchronization and in parallel in the above description. However, as long as the B-mode image and the orientation angle of the ultrasound probe 2 are acquired prior to transition to step S5, step S3 and step S4 are not necessarily performed in synchronization and in parallel. That is, after the B-mode image has been acquired in step S3, the orientation angle of the ultrasound probe 2 may be acquired in step S4. Alternatively, after the orientation angle of the ultrasound probe 2 has been acquired, the B-mode image may be acquired.

In addition, the calculation method of the orientation angle in the probe orientation angle detecting unit 10 is not limited to the above-described method as long as the orientation angle of the ultrasound probe 2 can be calculated. For example, although not illustrated, on the basis of positional information of the ultrasound probe 2 calculated by performing time quadrature twice, within a fixed time, on the acceleration detected by the orientation sensor 9, the orientation angle of the ultrasound probe 2 may be calculated in the probe orientation angle detecting unit 10.

In addition, although the use of the acceleration sensor has been illustrated as an example of the orientation sensor 9 that detects the operation of the ultrasound probe 2, another sensor may also be used as the orientation sensor 9 as long as the operation or the position of the ultrasound probe 2 is detected. As the orientation sensor 9 like this, for example, in addition to the acceleration sensor, a gyro sensor, a magnetic sensor, a GPS (Global Positioning System) sensor, or the like can be used. In addition, these sensors may be equipped with the ultrasound probe 2 or may be incorporated in the ultrasound probe 2.

For example, by using the gyro sensor that is attached to the ultrasound probe 2 as the orientation sensor 9, on the basis of an angular speed of the ultrasound probe 2 obtained from the gyro sensor, the orientation angle of the ultrasound probe 2 may also be detected from a known calculation method. In addition, for example, by using the magnetic sensor as the orientation sensor 9, on the basis of positional information of the ultrasound probe 2 detected by the magnetic sensor, the orientation angle of the ultrasound probe 2 may also be detected. Further, for example, by using the GPS sensor as the orientation sensor 9, on the basis of positional information of the ultrasound probe 2 acquired from the GPS sensor, the orientation angle of the ultrasound probe 2 may also be detected.

In addition, as long as the operation or the position of the ultrasound probe 2 is detected, the orientation sensor 9 is not necessarily equipped with or incorporated in the ultrasound probe 2, and may also be provided separately from the ultrasound probe 2. As the orientation sensor 9 like this, for example, although not illustrated, a known camera or the like may be used to detect positional information of the ultrasound probe 2, and on the basis of the detected positional information of the ultrasound probe 2, the orientation sensor 9 may also detect the orientation angle of the ultrasound probe 2.

In addition, although a case where the high frame rate at the time of the ultrasound diagnosis is set has been described as an example of the second imaging condition, another condition may also be set as the second imaging condition. For example, in a case where it is determined in step S6 that the part probability that the part included in the ultrasound image is the heart and the part probability that the part included in the ultrasound image is the right abdomen are greater than or equal to the threshold value, in order to clearly draw a characteristic pattern of the atria, the ventricles, the interventricular septum, and the like in the heart, a condition that increases the brightness of the ultrasound image may be set as the second imaging condition. The brightness of the ultrasound image may be increased by, for example, increasing a gain of the amplification unit 18 of the reception circuit 4. In addition, for example, the brightness of the ultrasound image may be increased by increasing a dynamic range in the A/D conversion unit 19 of the reception circuit 4. It is needless to say that the gain and the dynamic range can also be adjusted simultaneously. In addition, the brightness of the ultrasound image may also be increased by increasing the gain by increasing a driving voltage that the transmission circuit 5 outputs to the transducer array 2A of the ultrasound probe 2.

In addition, as the second imaging condition for clearly drawing the pattern of the part included in the ultrasound image, a condition that increases a resolution of the ultrasound image may also be used. The resolution can be increased by, for example, although not illustrated, increasing the number of ultrasound transducers of the transducer array 2A to be used at the time of the ultrasound diagnosis to increase a density of the ultrasound transducers to be used.

In this manner, in a case where at least one of the brightness or the resolution is increased as the second imaging condition in order to clearly draw the ultrasound image, for example, the image analyzing unit 13 easily performs pattern recognition using template matching, texture analysis, machine learning, or the like on the ultrasound image acquired by using the second imaging condition. On the basis of a result of the pattern recognition in the image analyzing unit 13, the part identifying unit 14 identifies the part included in the ultrasound image.

In the above description, mainly, a case has been described where the part probability that is determined by the apparatus control unit 15 to be greater than or equal to the threshold value in step S6 is the part probability that the part included in the ultrasound image is the heart and the part probability that the part included in the ultrasound image is the right abdomen. However, it is needless to say that the apparatus control unit 15 determines that the part probability that the part included in the ultrasound image is a part other than the heart and the right abdomen is greater than or equal to the threshold value. Since the orientation angle of the ultrasound probe 2 at the time of making an ultrasound diagnosis of lungs and the orientation angle of the ultrasound probe 2 at the time of making an ultrasound diagnosis of a urinary bladder are similar, for example, in a case where the apparatus control unit 15 determines that the part probability that the part included in the ultrasound image is lungs and the part probability that the part included in the ultrasound image is a urinary bladder are greater than or equal to the threshold value, the second imaging condition that decreases the frame rate at the time of the ultrasound diagnosis can be used. Since the lungs have a few structures as an organ and most of them is air, in a case of acquiring an ultrasound image of the lungs, there is a little change over time. On the other hand, since the urinary bladder has structures as an organ, there is a great change over time compared with the lungs. Thus, by setting a low frame rate, the change in the part between acquired ultrasound images can be made obvious.

In a case where a low frame rate at the time of the ultrasound diagnosis is set as the second imaging condition, the image analyzing unit 13 can, for example, calculate a movement amount (frame difference) of a pattern between ultrasound images acquired in a time-series manner by using the second imaging condition.

The part identifying unit 14 determines, for example, whether the frame difference calculated in the image analyzing unit 13 is greater than or equal to a fixed value. At this time, for example, if the frame difference is greater than or equal to the fixed value, the part identifying unit 14 identifies the part included in the ultrasound image as the urinary bladder, which is a part that changes to a great extent over time. On the other hand, if the frame difference is less than the fixed value, the part identifying unit 14 identifies the part included in the ultrasound image as lungs, which changes to a small extent over time. Note that the method of analysis between the ultrasound images performed in the image analyzing unit 13 on ultrasound images acquired by using the second imaging condition that sets the low frame rate at the time of the ultrasound diagnosis is not limited to the above-described calculation of the frame difference as long as it becomes easy to identify the part included in the ultrasound image. For example, a change rate of the frame difference may also be calculated, a change rate of an area of an edge structure of the part included in the ultrasound image may also be calculated, or a change rate of an area of pixels having a specific brightness in the ultrasound image may also be calculated.

In addition, although the B-mode image signal is generated from the reception signal output from the reception circuit 4 in the image generating unit 6 of the image acquiring unit 3, an imaging signal other than the B-mode image signal may also be generated from the reception signal. For example, although not illustrated, the B-mode processing unit 20 of the image generating unit 6 may be replaced by a processing unit that generates an M-mode (Motion mode) image signal, a color Doppler image signal, an elasticity image signal, or a sound speed map signal in order to generate the M-mode image signal, the color Doppler image signal, the elasticity image signal, or the sound speed map signal from the reception signal.

If the image signal other than the B-mode image signal is generated from the reception signal in this manner, image analysis in accordance with each type of image signal may also be performed. For example, if the M-mode image signal is generated from the reception signal, the image analyzing unit 13 may perform pattern recognition using template matching, texture analysis, machine learning, or the like, or time-series image analysis using optical flow.

In addition, for example, if the color Doppler image signal, the elasticity image signal, or the sound speed map signal is generated from the reception signal, the image analyzing unit 13 can analyze color information included in each image signal or the like.

In addition, the ultrasound diagnostic apparatus 1 described above is small, and thus may be a mobile ultrasound diagnostic apparatus that is used by being carried easily, or may be a stationary ultrasound diagnostic apparatus that is used by being provided in a consultation room or the like.

In addition, the ultrasound probe 2 is not particularly limited as long as an ultrasound beam can be transmitted/received to/from a subject, and may be of a sector type, a convex type, a linear type, or a radial type.

Second Embodiment

Figure 5:
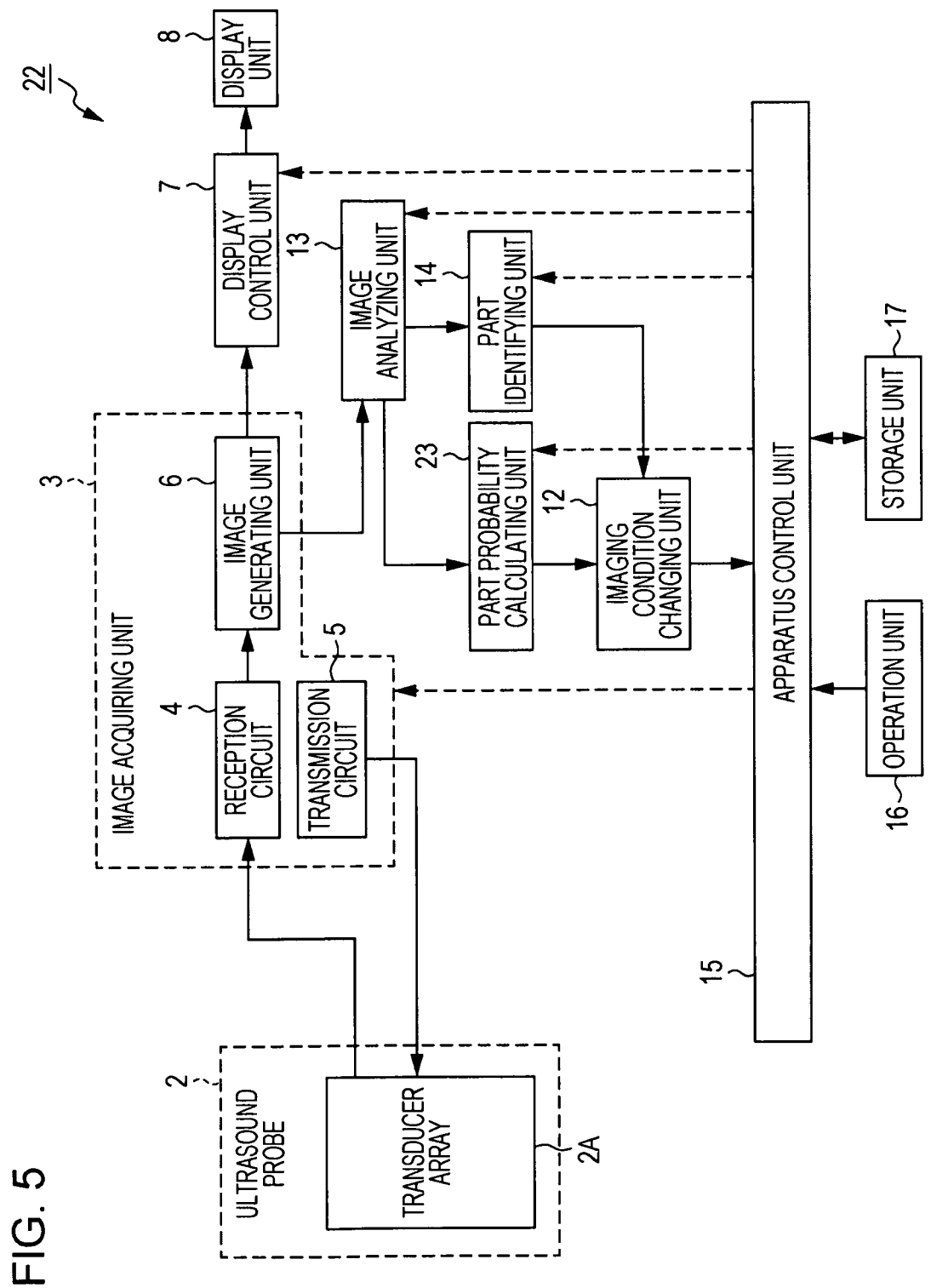
FIG. 5 is a block diagram illustrating a configuration of an ultrasound diagnostic apparatus according to a second embodiment.

FIG. 5 illustrates an ultrasound diagnostic apparatus 22 in a second embodiment. The ultrasound diagnostic apparatus 22 does not have the orientation sensor and the probe orientation angle detecting unit in the ultrasound diagnostic apparatus 1 in the first embodiment illustrated in FIG. 1 but has a part probability calculating unit 23 instead of the part probability calculating unit 11, and further, the image analyzing unit 13 is connected to the part probability calculating unit 23. The other configuration has the same components as those in the ultrasound diagnostic apparatus 1 illustrated in FIG. 1. Accordingly, in FIG. 5, the same components as those in FIG. 1 are denoted by the same reference numerals, and a detailed description of these components is omitted.

The part probability calculating unit 11 in the first embodiment calculates the probability that a part of a subject included in an ultrasound image is each specific part on the basis of the orientation angle of the ultrasound probe 2. However, the part probability calculating unit 23 in the second embodiment calculates the probability that a part of a subject included in an ultrasound image is each specific part on the basis of an image analysis result.

An operation of the ultrasound diagnostic apparatus 22 having such a configuration in the second embodiment will be described below with reference to a flowchart illustrated in FIG. 6.

Figure 4:
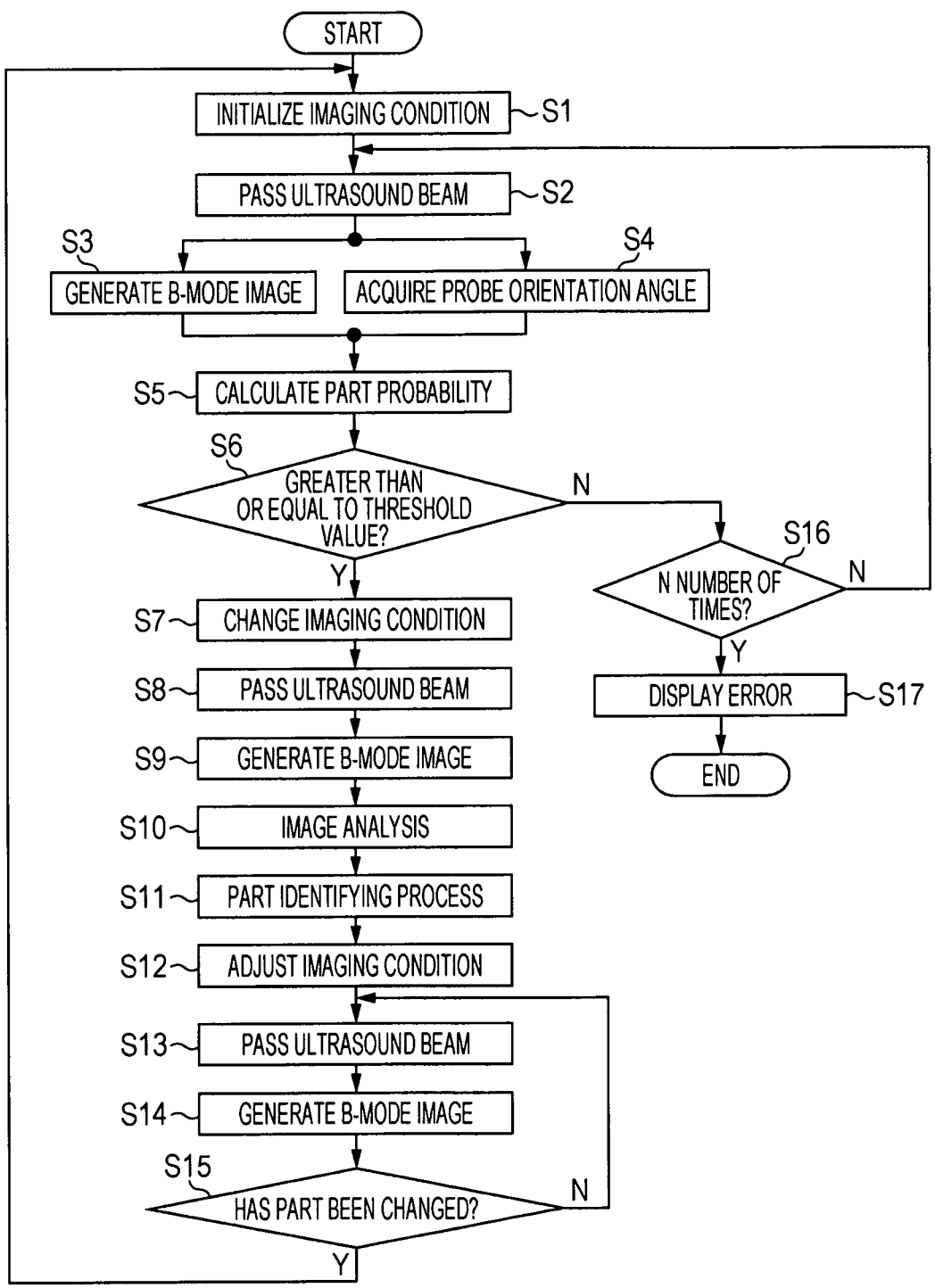
FIG. 4 is a flowchart of the first embodiment.

Step S1 to step S3 are the same as step S1 to step S3 in the first embodiment illustrated in FIG. 4 except that step S3 and step S4 are not performed in synchronization and in parallel. The imaging condition is initialized to the first imaging condition, and a B-mode image (ultrasound image) signal is generated from a reception signal acquired by transmitting/receiving and passing an ultrasound beam using the first imaging condition.

In step S18 subsequent to step S3, the apparatus control unit 15 determines whether acquisition of the ultrasound image by using the first imaging condition is a first time.

If, in step S18, the acquisition of an ultrasound image by using the first imaging condition is the first time, the process proceeds to step S19. In step S19, the image analyzing unit 13 performs image analysis on an ultrasound image of a single frame that has been output from the image generating unit 6 of the image acquiring unit 3. The image analysis performed on the ultrasound image of a single frame in step S19 is performed in order to narrow down candidate parts of a subject included in the ultrasound image from, for example, a plurality of diagnostic parts determined in eFAST testing. As such image analysis of the ultrasound image of a single frame, for example, the image analyzing unit 13 can detect an edge structure included in the ultrasound image of a single frame and can calculate an area (edge pixel area) of pixels of the edge structure oriented in a specific direction, which is, for example, an oblique direction.

Further, in step S20, on the basis of a result of the image analysis of the ultrasound image of a single frame in step S19, the part probability calculating unit 23 calculates a part probability that a part included in the ultrasound image is each specific part. Although various calculation methods can be used for the calculation of the part probability in the part probability calculating unit 23, for example, the part probability calculating unit 23 can calculate, as the part probability, a reciprocal of a difference between an area (target edge pixel area) of pixels of the edge structure oriented in the specific direction, which is a target for each specific part of the subject, and the actual edge pixel area calculated in step S19. In this case, the part probability calculating unit 23 calculates the probability that the part included in the ultrasound image is each specific part by using the target edge pixel area for each part of the subject.

In the subsequent step S6, as in step S6 in the first embodiment, the apparatus control unit 15 determines whether the part probability calculated in step S20 is greater than or equal to a predetermined threshold value. As for the threshold value used for the determination of the part probability, for example, it is preferable that only the part probabilities for parts where the edge pixel areas, that is, the target edge pixel areas, are similar be greater than or equal to the threshold value. For example, if edge structure detection is performed through image analysis, a large number of oblique edge structures are detected in both the ultrasound image of the heart and the ultrasound image of the right abdomen. Thus, the target edge pixel areas for the heart and the right abdomen are similar. On the other hand, since the lungs have a small number of structures as an organ, there are a small number of oblique edge structures even if the edge structure detection is performed through image analysis, and the target edge pixel areas of the heart and the right abdomen are not similar. Thus, the lungs can be distinguished from the heart and the right abdomen.

If it is determined in step S6 that at least one part probability among a plurality of part probabilities calculated by the part probability calculating unit 23 is greater than or equal to the threshold value, the process proceeds to step S7. Step S7 to step S15 are the same as step S7 to step S15 in the first embodiment illustrated in FIG. 4, and the first imaging condition is changed to the second imaging condition on the basis of the part probability, and then, the ultrasound image that is further acquired is subjected to image analysis, and thereby the part of the subject included in the ultrasound image is identified. Subsequently, the second imaging condition is changed to the third imaging condition that is appropriate for the identified part, and the ultrasound image is further acquired by using the third imaging condition. The ultrasound image is further acquired until the diagnostic part is changed, and when the diagnostic part is changed, the process returns to step S1.

If it is determined in step S6 that the plurality of part probabilities calculated by the part probability calculating unit 23 are all less than the threshold value, the process returns to step S2. When the ultrasound image is acquired in second-time step S2 and step S3, in the subsequent step S18, the apparatus control unit 15 determines that the acquisition of the ultrasound image is not the first time, and the process proceeds to step S21.

In step S21, the image analyzing unit 13 performs image analysis on ultrasound images of a plurality of frames that are output from the image generating unit 6 of the image acquiring unit 3. As in the image analysis of the ultrasound image of a single frame in step S19, the image analysis of the ultrasound images of a plurality of frames performed in step S21 is performed in order to narrow down candidate parts of a subject included in the ultrasound images from a plurality of diagnostic parts. As such image analysis of the ultrasound images of a plurality of frames, for example, image analysis using so-called optical flow can be performed on the ultrasound image acquired by using the first imaging condition.

In the subsequent step S22, on the basis of a result of the image analysis of the ultrasound images of a plurality of frames in step S21, the part probability calculating unit 23 calculates the part probability. The part probability calculating unit 23 can calculate, as the part probability, for example, a reciprocal of a difference between the number of vectors (target number of vectors) mapped in the optical flow, which is a target for each specific part of the subject, and the actual number of vectors (number of vectors) calculated in step S21. In this case, by using the target number of vectors for each part of the subject, the part probability calculating unit 23 calculates the probabilities that the part included in the ultrasound images is each specific part.

Note that in this case, since the ultrasound image(s) is acquired by using the frame rate of the first imaging condition, although it is possible to distinguish between a part with much movement and a part with a little movement by calculating the part probability, there is also a part that is not explicitly distinguished. For example, since the heart has beats, a large number of vectors are mapped in an ultrasound image of the heart by the optical flow. In addition, the abdomen includes a large number of structures as an organ and the ultrasound probe 2 is moved by an operator at the time of an ultrasound diagnosis, and thus, a large number of vectors are mapped due to the movement of the ultrasound probe 2 in an ultrasound image of the abdomen. On the other hand, for example, as for the lungs, there are a small number of structures as an organ and the ultrasound probe 2 is rarely moved by an operator at the time of the ultrasound diagnosis, and thus, the number of vectors mapped by the optical flow is small in an ultrasound image of the lungs. Accordingly, for example, by calculation of the part probability based on the optical flow for the ultrasound image obtained by using the first imaging condition, it is possible to distinguish between the heart and the abdomen, which are the parts with much movement, and the lungs, which are the parts with a little movement.

In step S23, as in step S6, the apparatus control unit 15 determines whether the part probability obtained in step S22 is greater than or equal to the threshold value.

If it is determined in step S23 that the plurality of part probabilities calculated on the basis of the result of image analysis of the ultrasound images of a plurality of frames are all less than the threshold value, the process proceeds to step S16.

As in step S16 in the first embodiment illustrated in FIG. 4, in step S16, it is determined whether the number of times of determination in step S23 that the plurality of part probabilities are all less than the threshold value is N. At this time, if the number of times of determination in step S23 that the plurality of part probabilities are all less than the threshold value is less than N, the process returns to step S2. Subsequently, when the number of times of determination that the plurality of part probabilities are all less than the threshold value becomes N in step S23, an error is displayed in the display unit 8 in step S17, and the ultrasound diagnostic apparatus 22 terminates the operation.

On the other hand, if it is determined in step S23 that at least one of the plurality of part probabilities calculated on the basis of the result of image analysis of the ultrasound images of a plurality of frames is greater than or equal to the threshold value, the process proceeds to step S7.

As described above, according to the ultrasound diagnostic apparatus 22 in the second embodiment illustrated in FIG. 5, the part probability is calculated on the basis of the analysis result of the ultrasound image(s), the first imaging condition is changed to the second imaging condition on the basis of the part probability, and the ultrasound image is further acquired by using the second imaging condition. Accordingly, as in the ultrasound diagnostic apparatus 1 in the first embodiment illustrated in FIG. 1, by acquiring the ultrasound image twice separately, the ultrasound diagnostic apparatus 22 in the second embodiment illustrated in FIG. 5 can narrow down candidate parts for identification, and thus, the part can be finely identified so as to set an appropriate imaging condition. In addition, on the basis of the image analysis result using the ultrasound image of a single frame or the image analysis result using the ultrasound images of a plurality of frames, the part probability calculating unit 23 can calculate the part probability, that is, calculate the part probability by using characteristics of the structure of the part or the movement of the part. Accordingly, an accurate part probability can be calculated by using image analysis that is appropriate for the part.

In addition, although a case where detection of the edge structure included in the ultrasound image is used as a method of image analysis using the ultrasound image of a single frame has been described, a method of image analysis such as detection of a high-brightness pixel or pattern recognition such as template matching can also be used.

For example, in a case where a high-brightness pixel is detected as image analysis using the ultrasound image of a single frame, in step S19, the image analyzing unit 13 can calculate the area (high-brightness pixel area) of pixels having a fixed brightness or higher included in the ultrasound image. In the subsequent step S20, for example, the part probability calculating unit 23 can calculate, as the part probability, a reciprocal of a difference between a target high-brightness pixel area (target high-brightness pixel area) for each diagnostic part and the actual high-brightness pixel area calculated in step S19.

In addition, for example, in a case where pattern recognition such as template matching is performed as image analysis using the ultrasound image of a single frame, in step S19, the image analyzing unit 13 can calculate, as a score, a degree of similarity between a template of each diagnostic part and a part included in the actual ultrasound image. In the subsequent step S20, for example, the part probability calculating unit 23 can calculate, as the part probability, a reciprocal of a difference between a target degree of similarity score (target score) for each diagnostic part and the actual score calculated in step S19.

In addition, although a case where the optical flow is used as the method of image analysis using the ultrasound images of a plurality of frames has been described, another analysis method can also be used. For example, as such a method of image analysis, the image analyzing unit 13 can track a specific high-brightness point of a part included in each of the ultrasound images of a plurality of frames in a time-series manner to calculate a period for reciprocation of the high-brightness point. In this case, for example, the part probability calculating unit 23 can calculate, as the part probability, a reciprocal of a difference between a period of a target high-brightness point for each diagnostic part and a period of the calculated actual high-brightness point.

Third Embodiment

Figure 7:
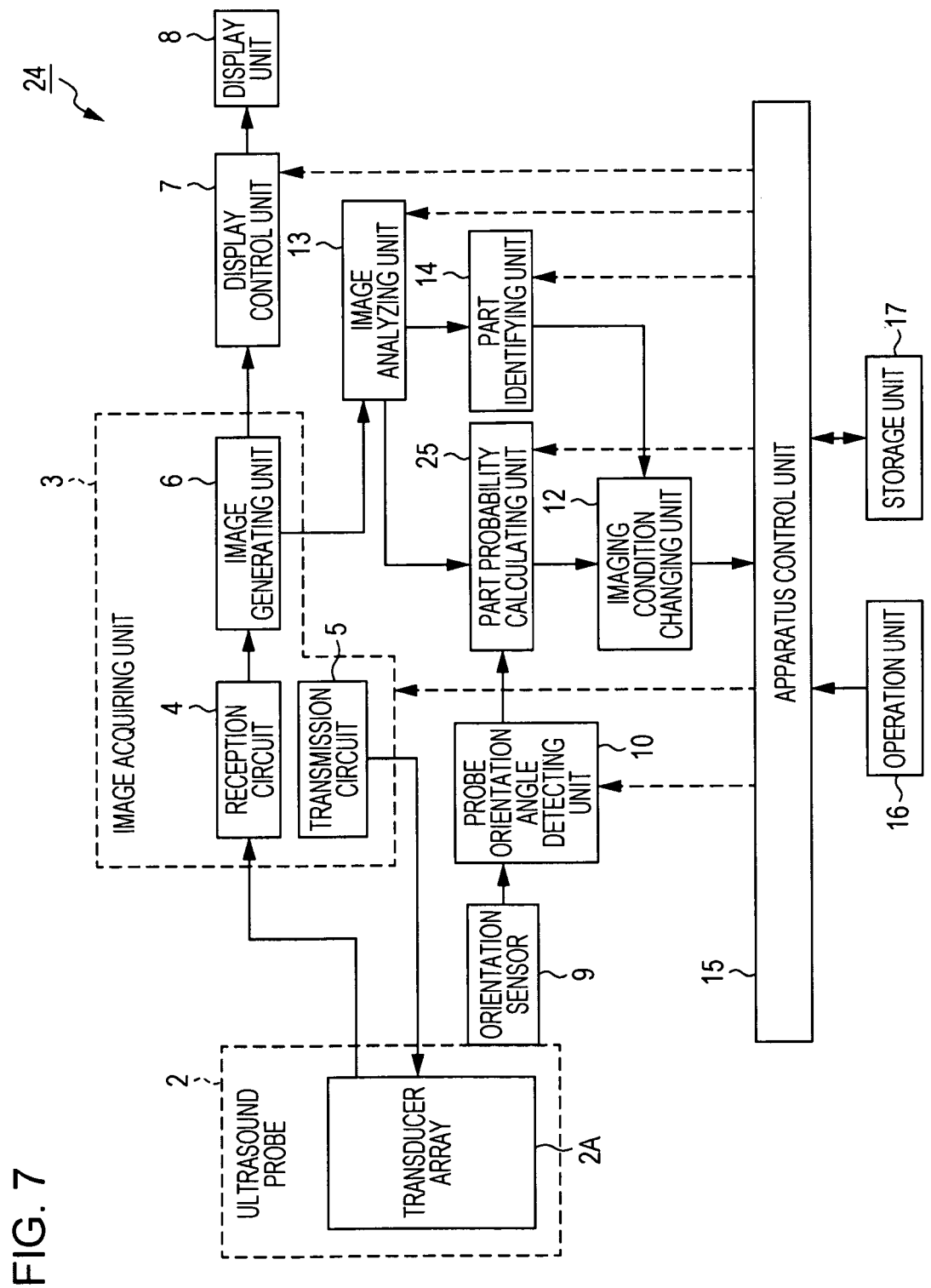
FIG. 7 is a block diagram illustrating a configuration of an ultrasound diagnostic apparatus according to a third embodiment.

FIG. 7 illustrates an ultrasound diagnostic apparatus 24 in a third embodiment. The ultrasound diagnostic apparatus 24 has the same components as those in the ultrasound diagnostic apparatus 1 illustrated in FIG. 1 except that the part probability calculating unit 11 of the ultrasound diagnostic apparatus 1 in the first embodiment illustrated in FIG. 1 is replaced with a part probability calculating unit 25 and that the part probability calculating unit 25 is connected to the image analyzing unit 13. Therefore, the same components as those in FIG. 1 are denoted by the same reference numerals in FIG. 7, and a detailed description of these components is omitted.

By the way, the part probability calculating unit 11 in the first embodiment illustrated in FIG. 1 calculates the part probability only on the basis of the orientation angle of the ultrasound probe 2, and the part probability calculating unit 23 in the second embodiment illustrated in FIG. 5 calculates the part probability only on the basis of the result of image analysis. In contrast, the part probability calculating unit 25 in the third embodiment calculates the part probability by integrating the orientation angle of the ultrasound probe 2 and the result of image analysis.

Figure 8:
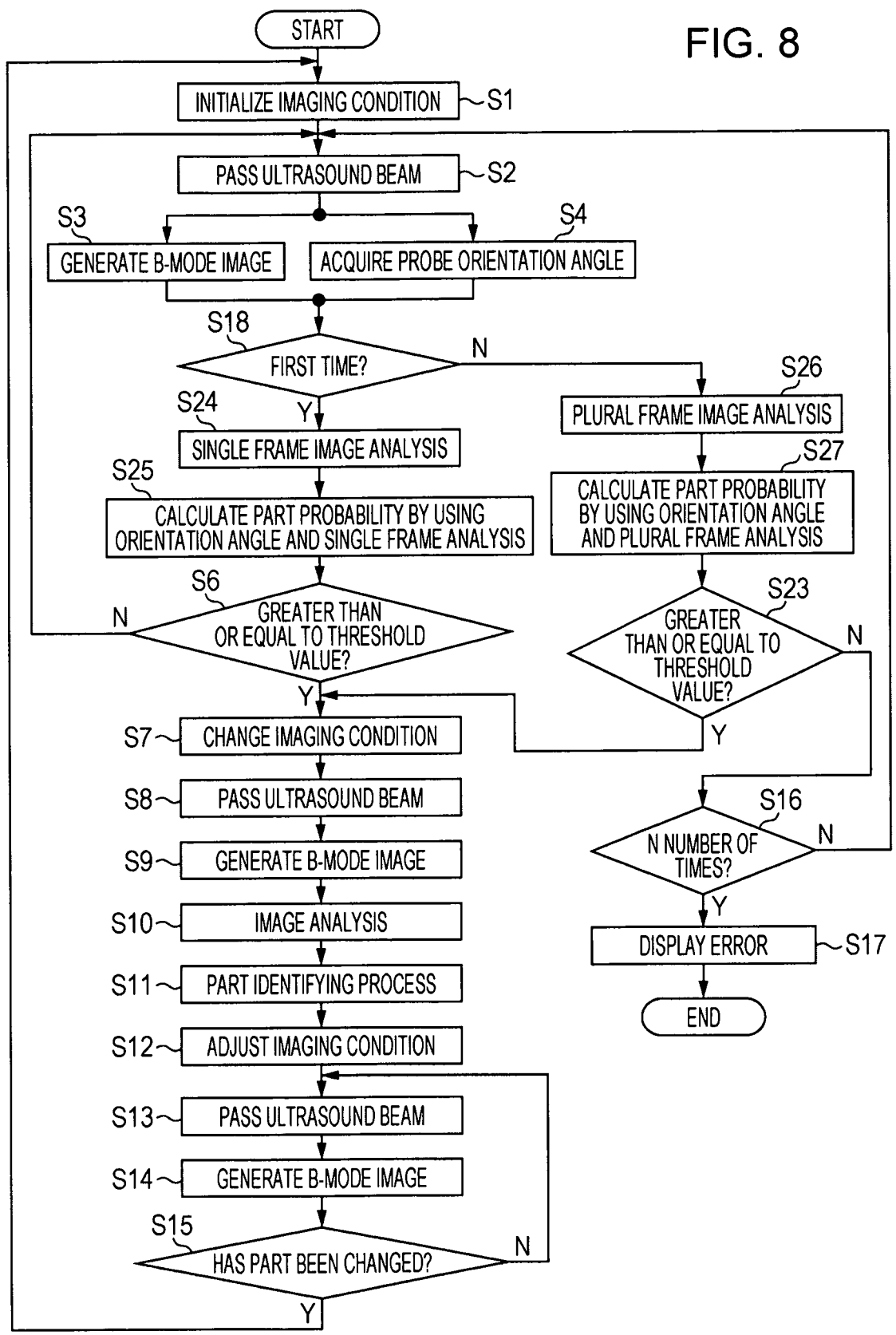
FIG. 8 is a flowchart of the third embodiment.

An operation of the ultrasound diagnostic apparatus 24 having such a configuration in the third embodiment will be described below with reference to a flowchart illustrated in FIG. 8.

Step S1 to step S4 are the same as step S1 to step S4 in the first embodiment illustrated in FIG. 4. The imaging condition is initialized to the first imaging condition. A B-mode image (ultrasound image) is generated from a reception signal acquired by transmitting/receiving and passing an ultrasound beam using the first imaging condition. In synchronization with the generation of the B-mode image, the orientation angle of the ultrasound probe 2 is detected.

In addition, step S18 subsequent to step S3 and step S4 is the same as step S18 in the second embodiment illustrated in FIG. 5. The apparatus control unit 15 determines whether acquisition of the ultrasound image by using the first imaging condition is a first time.

If it is determined in step S18 that the acquisition of the ultrasound image by using the first imaging condition is the first time, the process proceeds to step S24. In step S24, the image analyzing unit 13 performs image analysis on an ultrasound image of a single frame acquired by using the first imaging condition. The method of image analysis of the ultrasound image of a single frame in step S24 is the same as the method of image analysis of the ultrasound image of a single frame described in step S19 in the second embodiment.

In the subsequent step S25, the part probability calculating unit 25 calculates each of a part probability based on the orientation angle of the ultrasound probe 2 detected in step S24 and a part probability based on a result of image analysis of the ultrasound image of a single frame. The method of calculating the part probability based on the orientation angle of the ultrasound probe 2 is the same as the calculation method described in step S5 in the first embodiment, and the method of calculating the part probability based on the result of image analysis of the ultrasound image of a single frame is the same as the calculation method described in step S20 in the second embodiment. In step S25, the part probability calculating unit 25 further integrates the part probability based on the orientation angle of the ultrasound probe 2 and the part probability based on the result of image analysis of the ultrasound image of a single frame to calculate each part probability that a part included in the ultrasound image is each specific part. Although various methods can be used as such a method of integrating the part probabilities calculated by two types of calculation methods, for example, as each part probability, it is possible to calculate, for each part serving as a candidate diagnostic part, an average of the part probability based on the orientation angle of the ultrasound probe 2 and the part probability based on the result of image analysis of the ultrasound image of a single frame.

In step S6 subsequent to step S25, as in step S6 in the first embodiment illustrated in FIG. 4, it is determined whether the part probability calculated in step S25 is greater than or equal to a predetermined threshold value.

If, in step S6, at least one of the plurality of calculated part probabilities is greater than or equal to the threshold value, the process proceeds to step S7. Step S7 to step S15 are the same as step S7 to step S15 in the first embodiment illustrated in FIG. 4, and a detailed description thereof is omitted.

If, in step S6, the plurality of calculated part probabilities are all less than the threshold value, the process returns to step S2. When the ultrasound image is acquired by using the first imaging condition in second-time step S2 and step S3, in the subsequent step S18, it is determined that the acquisition of the ultrasound image by using the first imaging condition is not the first time, and the process proceeds to step S26.

In step S26, the image analyzing unit 13 performs image analysis on ultrasound images of a plurality of frames acquired by using the first imaging condition. The method of image analysis of the ultrasound images of a plurality of frames in step S26 is the same as the method of image analysis of the ultrasound images of a plurality of frames described in step S21 in the second embodiment.

In step S27, the part probability calculating unit 25 calculates each of the part probability based on the orientation angle of the ultrasound probe 2 detected in step S26 and the part probability based on a result of the image analysis of the ultrasound images of a plurality of frames. The method of calculating the part probability based on the orientation angle of the ultrasound probe 2 is the same as the calculation method described in step S5 in the first embodiment, and the method of calculating the part probability based on the result of image analysis of the ultrasound images of a plurality of frames is the same as the calculation method described in step S22 in the second embodiment. In step S26, the part probability calculating unit 25 further integrates the part probability based on the orientation angle of the ultrasound probe 2 and the part probability based on the result of image analysis of the ultrasound images of a plurality of frames to calculate each part probability that a part included in the ultrasound image is each specific part. As in the method described in step S25, various methods can be used as such a method of integrating the part probabilities calculated by two types of calculation methods.

Figure 6:
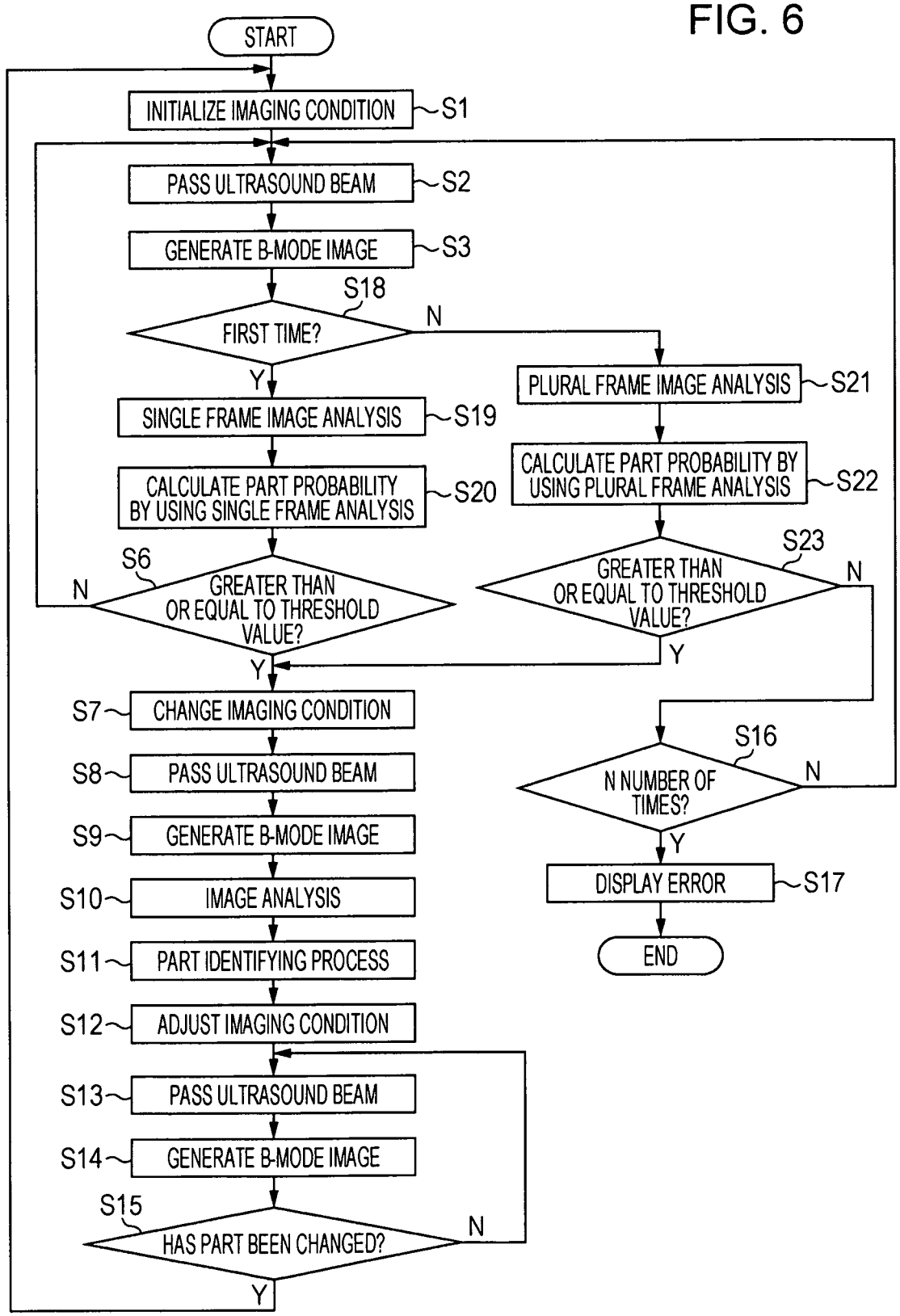
FIG. 6 is a flowchart of the second embodiment.

In step S23 subsequent to step S27, as in step S23 in the second embodiment illustrated in FIG. 6, it is determined whether the part probability calculated in step S27 is greater than or equal to the threshold value.

If, in step S23, the plurality of calculated part probabilities are all less than the threshold value, the process proceeds to step S16.

As in step S16 in the first embodiment illustrated in FIG. 4, in step S16, the apparatus control unit 15 determines whether the number of times of determination in step S23 that the plurality of part probabilities are all less than the threshold value is N. If it is determined in step S16 that the number of times of determination that the plurality of part probabilities are all less than the threshold value is less than N, the process returns to step S2. Subsequently, when the number of times of determination that the plurality of part probabilities are all less than the threshold value becomes N in step S16, an error is displayed in the display unit 8 in step S17, and the ultrasound diagnostic apparatus 24 terminates the operation.

If, in step S23, at least one of the plurality of calculated part probabilities is greater than or equal to the threshold value, the process proceeds to step S7.

As described above, with the ultrasound diagnostic apparatus 24 in the third embodiment illustrated in FIG. 7, the part probability is calculated on the basis of each of the orientation angle of the ultrasound probe 2 and the result of image analysis of the ultrasound image, the first imaging condition is changed to the second imaging condition on the basis of the part probability, and the ultrasound image is further acquired by using the second imaging condition. Accordingly, as in the ultrasound diagnostic apparatus 1 in the first embodiment illustrated in FIG. 1, by acquiring the ultrasound image twice separately, the ultrasound diagnostic apparatus 24 in the third embodiment illustrated in FIG. 7 can narrow down candidate parts for identification, and thus, the part can be finely identified so as to set an appropriate imaging condition. In addition, since the part probability can be calculated by taking into account both of the part probability calculated on the basis of the orientation angle of the ultrasound probe 2 and the part probability calculated by using the result of image analysis, the part probability calculating unit 25 can calculate a part probability that is more accurate than a part probability calculated by using only one of the orientation angle of the ultrasound probe 2 and the result of image analysis.

In addition, as a method of integrating the part probability calculated on the basis of the orientation angle of the ultrasound probe 2 and the part probability calculated on the basis of the result of image analysis, an average of the part probabilities is used in the above description, another method can also be used.

For example, the part probability calculating unit 25 can weight at least one of the part probability calculated on the basis of the orientation angle of the ultrasound probe 2 and the part probability calculated on the basis of the result of image analysis to calculate the average of the part probabilities. By weighting the part probability in this manner, a priority can be given to a part probability calculation method that is appropriate for each part, and thus, the accuracy of the part probability for each part can be increased.

In addition, for example, the part probability calculating unit 25 can use as the part probability a higher part probability of the part probability calculated on the basis of the orientation angle of the ultrasound probe 2 and the part probability calculated on the basis of the result of image analysis. In this case, a part probability calculated by using a more appropriate calculation method for each part of the part probability calculated on the basis of the orientation angle of the ultrasound probe 2 and the part probability calculated on the basis of the result of image analysis can be used.

The ultrasound diagnostic apparatus according to the present invention has been described above in detail. However, the present invention is not limited to the above examples, and it is needless to say that various kinds of improvement and modification may be made without departing from the spirit of the present invention. In addition, the plurality of embodiments and examples illustrated in the above description may be used in appropriate combination.

REFERENCE SIGNS LIST 1, 22, 24 ultrasound diagnostic apparatus
2 ultrasound probe
2A transducer array
3 image acquiring unit
4 reception circuit
5 transmission circuit
6 image generating unit
7 display control unit
8 display unit 9 orientation sensor
10 probe orientation angle detecting unit
11, 23, 25 part probability calculating unit
12 imaging condition changing unit
13 image analyzing unit
14 part identifying unit
15 apparatus control unit
16 operation unit
17 storage unit
18 amplification unit
19 A/D conversion unit
20 B-mode processing unit
21 image processing unit

What is claimed is:

1. An ultrasound diagnostic apparatus comprising:
an ultrasound probe; and
a central processing unit and an operating program for operating the central processing unit configured to transmit an ultrasound beam from the ultrasound probe toward a subject,
receive the ultrasound beam in accordance with a set imaging condition to acquire an ultrasound image,
calculate, for the ultrasound image acquired in accordance with a first imaging condition, a probability that a part of the subject included in the ultrasound image is each of a plurality of predetermined parts of the subject from at least one of orientation angles of the ultrasound probe or an analysis result of the ultrasound image,
change, when two or more probabilities among the plurality of probabilities calculated for the plurality of predetermined parts are greater than or equal to a predetermined threshold value, the first imaging condition to a second imaging condition for identifying which of two or more parts corresponding to the two or more probabilities is the part of the subject included in the ultrasound image acquired by using the first imaging condition, and
acquire an ultrasound image by using the second imaging condition.

2. The ultrasound diagnostic apparatus according to claim 1, wherein the central processing unit and the operating program are configured to further calculate the probability on the basis of the orientation angle and the analysis result of the ultrasound image acquired by using the first imaging condition.

3. The ultrasound diagnostic apparatus according to claim 2, wherein the ultrasound image acquired by using the first imaging condition consists of a single frame.

4. The ultrasound diagnostic apparatus according to claim 3, wherein the central processing unit and the operating program are configured to further identify the part of the subject for which the probability has been calculated on the basis of an analysis result of the ultrasound image being further acquired by the second imaging condition.

5. The ultrasound diagnostic apparatus according to claim 2,
wherein the ultrasound image acquired by the first imaging condition consists of a plurality of frames of the part of the subject and the analysis result is of a movement of a specific pattern found in common within the plurality of frames of the part of the subject.

6. The ultrasound diagnostic apparatus according to claim 2, wherein the central processing unit and the operating program are configured to further identify the part of the subject for which the probability has been calculated on the basis of an analysis result of the ultrasound image being further acquired by the second imaging condition.

7. The ultrasound diagnostic apparatus according to claim 1, further comprising:
an orientation sensor device configured to detect an acceleration or an angular speed or a position of the ultrasound probe,
wherein the central processing unit and the operating program for operating the central processing unit are configured to
detect the orientation angle corresponding to the ultrasound image acquired by using the first imaging condition on the basis of a signal of the orientation sensor device, and
calculate the probability on the basis of the orientation angle.

8. The ultrasound diagnostic apparatus according to claim 7,
wherein the central processing unit and the operating program are configured to further analyze the ultrasound image acquired by using the second imaging condition.

9. The ultrasound diagnostic apparatus according to claim 8, wherein the central processing unit and the operating program are configured to further identify the part of the subject for which the probability has been calculated on the basis of an analysis result of the ultrasound image being further acquired by the second imaging condition.

10. The ultrasound diagnostic apparatus according to claim 1,
wherein the central processing unit and the operating program are configured to
analyze the ultrasound image acquired by using the first imaging condition, and
calculate the probability on the basis of the analysis result for the ultrasound image acquired by using the first imaging condition.

11. The ultrasound diagnostic apparatus according to claim 10, wherein the ultrasound image acquired by using the first imaging condition consists of a single frame.

12. The ultrasound diagnostic apparatus according to claim 11, wherein the central processing unit and the operating program are configured to further identify the part of the subject for which the probability has been calculated on the basis of an analysis result of the ultrasound image being further acquired by the second imaging condition.

13. The ultrasound diagnostic apparatus according to claim 10,
wherein the ultrasound image acquired by the first imaging condition consists of a plurality of frames of the part of the subject and the analysis result is of a movement of a specific pattern found in common within the plurality of frames of the part of the subject.

14. The ultrasound diagnostic apparatus according to claim 13, wherein the central processing unit and the operating program are configured to further identify the part of the subject for which the probability has been calculated on the basis of an analysis result of the ultrasound image being further acquired by the second imaging condition.

15. The ultrasound diagnostic apparatus according to claim 10, wherein the central processing unit and the operating program are configured to further identify the part of the subject for which the probability has been calculated on the basis of an analysis result of the ultrasound image being further acquired by the second imaging condition.

16. A control method of an ultrasound diagnostic apparatus, comprising:

transmitting an ultrasound beam from an ultrasound probe toward a subject and receiving the ultrasound beam in accordance with a set imaging condition to acquire an ultrasound image;

calculating, for the ultrasound image acquired in accordance with a first imaging condition, a probability that a part of the subject included in the ultrasound image is each of a plurality of predetermined parts of the subject from at least one of orientation angles of the ultrasound probe or an analysis result of the first ultrasound image;

changing, when two or more probabilities among the plurality of probabilities calculated for the plurality of predetermined parts are greater than or equal to a predetermined threshold value, the first imaging condition to a second imaging condition for identifying which of two or more parts corresponding to the two or more probabilities is the part of the subject included in the ultrasound image acquired by using the first imaging condition; and further acquiring an ultrasound image by using the second imaging condition.

\* \* \* \* \*